(12) United States Patent
Bavar

(10) Patent No.: US 8,105,081 B2
(45) Date of Patent: Jan. 31, 2012

(54) SURGICAL DRILL GUIDE AND INDEX SYSTEM

(76) Inventor: Trevor Bavar, Yonkers, NY (US)

( * ) Notice: Subject to any disclaimer, the term of this patent is extended or adjusted under 35 U.S.C. 154(b) by 720 days.

(21) Appl. No.: 12/154,692

(22) Filed: May 23, 2008

(65) Prior Publication Data

US 2009/0011382 A1    Jan. 8, 2009

Related U.S. Application Data

(60) Provisional application No. 60/931,901, filed on May 25, 2007.

(51) Int. Cl.
*A61C 19/04* (2006.01)
*A61C 3/00* (2006.01)

(52) U.S. Cl. .......................... 433/75; 433/215

(58) Field of Classification Search .......... 433/172–176, 433/201.1, 72–76, 215; 606/96, 80; 408/241 G, 408/97
See application file for complete search history.

(56) References Cited

U.S. PATENT DOCUMENTS

| | | | |
|---|---|---|---|
| 5,133,660 A | 7/1992 | Fenick | |
| 5,183,414 A | 2/1993 | Czerniawski | |
| 5,595,703 A | 1/1997 | Swaelens et al. | |
| 5,613,970 A * | 3/1997 | Houston et al. | 606/88 |
| 5,718,579 A * | 2/1998 | Kennedy | 433/75 |
| 5,768,134 A | 6/1998 | Swaelens et al. | |
| 5,967,777 A | 10/1999 | Klein et al. | |
| 6,361,318 B1 | 3/2002 | Back et al. | |
| 6,514,258 B1 | 2/2003 | Brown et al. | |
| 6,814,575 B2 | 11/2004 | Poirier | |
| 6,821,123 B2 | 11/2004 | Andersson et al. | |
| 6,848,909 B1 | 2/2005 | Persson | |
| 6,902,401 B2 | 6/2005 | Jorneus et al. | |
| 7,294,133 B2 * | 11/2007 | Zink et al. | 606/96 |
| 2007/0288007 A1 * | 12/2007 | Burkus et al. | 606/61 |
| 2008/0124676 A1 * | 5/2008 | Marotta | 433/174 |

(Continued)

FOREIGN PATENT DOCUMENTS

EP    1 532 939 A1    5/2005

(Continued)

OTHER PUBLICATIONS

Nobel Guide—Procedures and Products Powered by Procera @ Nobel Biocare Services AG, 2003.

(Continued)

*Primary Examiner* — Todd Manahan
*Assistant Examiner* — Yogesh Patel
(74) *Attorney, Agent, or Firm* — Abelman, Frayne & Schwab

(57) ABSTRACT

A surgical drill guide for installing dental implants with predetermined angular alignment and rotational orientation for a dental prosthesis, formed of: a. a base part formed to correspond generally to the shape and contour of a patient's upper or lower mouth, the base part having peripheral edges and having opposite tissue and mouth sides and at least one drill guide hole extending through the base part from the tissue side to the mouth side, each of the drill guide holes having a central axis at a predetermined angular orientation relative to the mouth side and having lateral location relative to the peripheral edges, and b. a set of rotational position indicators on the tissue and mouth sides respectively of the base part for each of the drill guide holes, the rotational position indicators of each set being at the same rotational position about the central axis of the drill guide hole.

7 Claims, 9 Drawing Sheets

U.S. PATENT DOCUMENTS

2008/0153060 A1   6/2008   De Moyer

FOREIGN PATENT DOCUMENTS

| | | |
|---|---|---|
| FR | 2 808 669 A1 | 11/2001 |
| WO | WO 03/073954 A1 | 9/2003 |
| WO | WO 2004/017860 A1 | 3/2004 |
| WO | WO 2004/075771 A | 9/2004 |

OTHER PUBLICATIONS

Nobel Guide—Procedures and Products Powered by Procera @ Nobel Biocare Services AG, 2005.

* cited by examiner

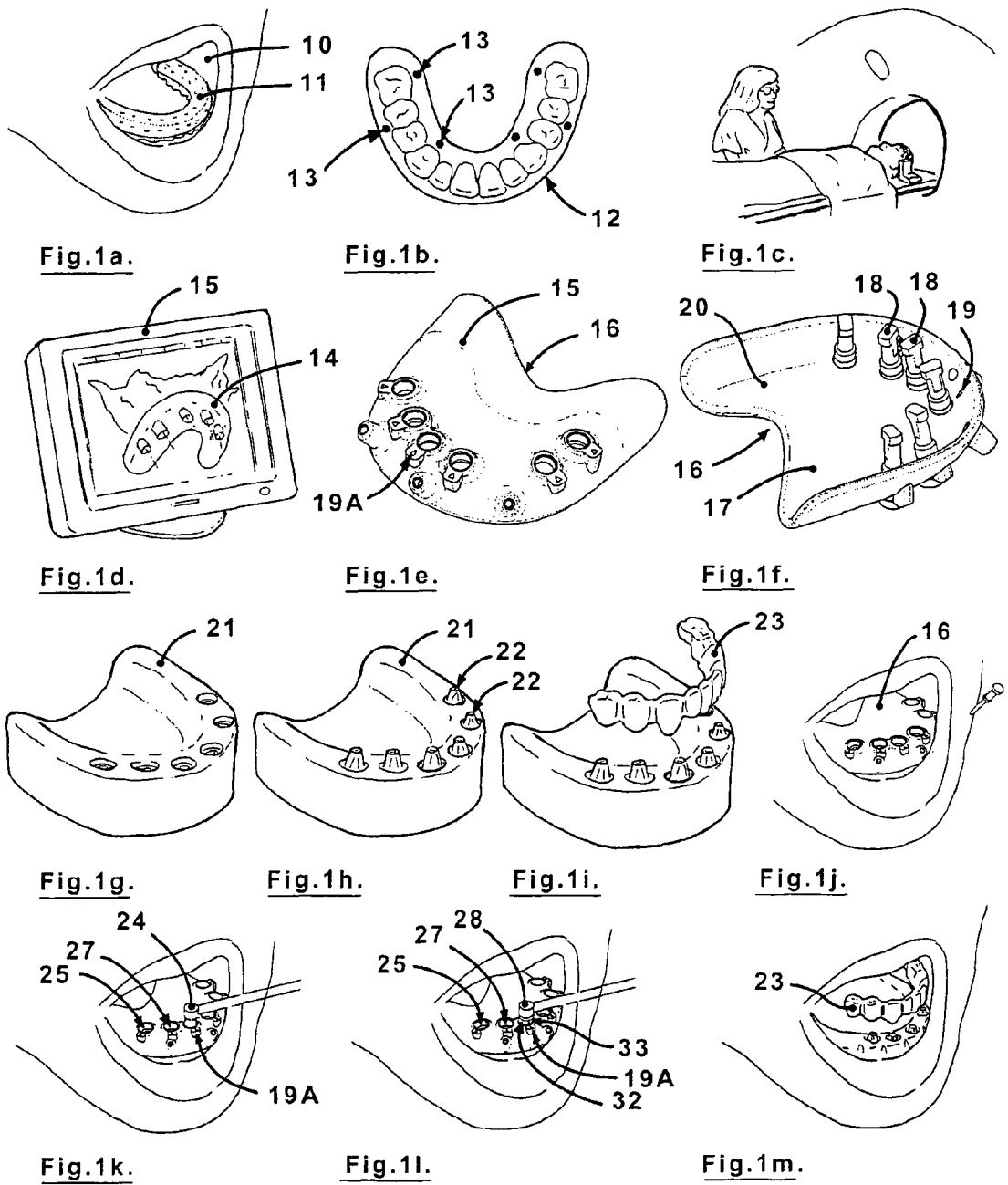

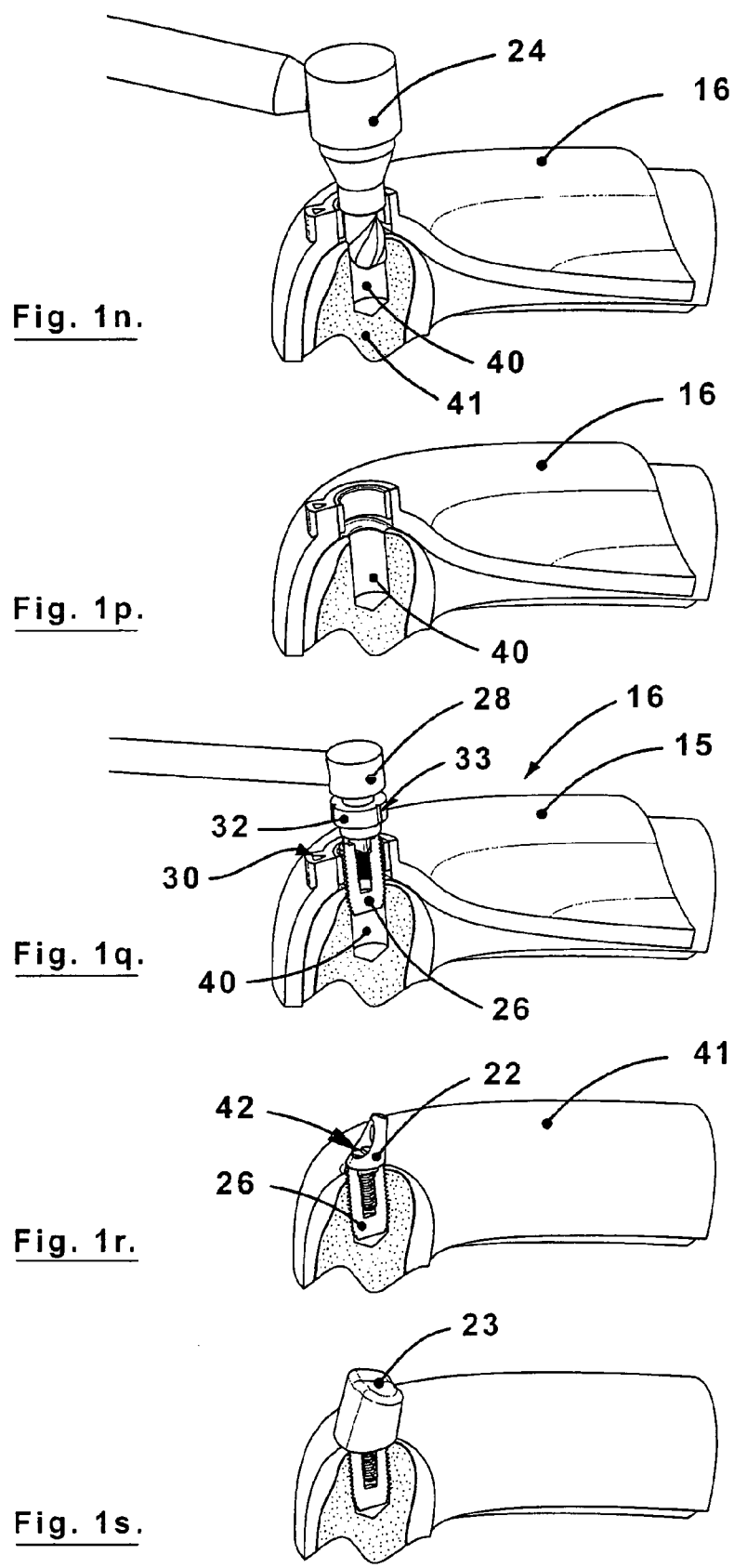

SURGICAL DRILL GUIDE AND INDEX SYSTEM

This application claims priority on Provisional Application No. 60/931,901 filed May 25, 2007 which is incorporated by reference herein.

I. BACKGROUND OF THE INVENTION

A. Field of the Invention

This invention is in the field of dental prostheses and methods and apparatus for manufacturing dental prostheses and for installing dental prostheses in a patient's mouth.

B. Prior Art Patents and Publication

"NobelGuide—Procedures & Products Powered by Procera®" ©Nobel Biocare Services AG 2005, U.S. Pat. Nos. 5,595,703; 5,768,134; 6,361,318; 6,821,123; 6,848,909; and 6,902,401.

C. Prior Art Procedures and Apparatus

1. In describing prior art procedures and apparatus the following terminology and definitions are commonly used.

Dental Prosthesis means an artificial tooth or a series of artificial teeth that is used to cosmetically and functionally restore missing or damaged teeth in a patient.

Implant means a structure that is implanted in a patient's bone as an anchor for a dental prosthesis. The typical dental implant is an externally threaded cylinder that is placed into a hole that is drilled into a patient's bone. The top of the implant has a collar part to receive an abutment.

Abutment means a structure that is attached to an implant to create a mounting feature for a prosthesis.

Angled abutment means a type of abutment that allows a prosthesis to be fixed to a patient's mouth, along an axis that differs from the axis of the implant.

Model means a casting of a patient's mouth that is used to select or construct abutments, and prosthesis.

Transfer post means a device that is inserted into an implant that has been placed in a patient's mouth. It is used to record the position of implants to facilitate the construction of a model.

Analog means a device that is used to simulate a dental implant in a cast model of a patient's teeth.

Surgical guide means a fixture that is used by a surgeon to aid in the positioning of drilled holes for placing implants. It can also be used to position analogs during the construction of a model.

Analog Mount means a device that is used to temporarily position an analog in a surgical guide during the model casting process.

Implant Driver means a tool that is used to screw implants into a patient's bone Fixture Mount means a device that is inserted into the implant and used to accurately pilot an implant through the surgical guide during surgery. It is rotated by an implant driver.

Tissue side and mouth side of the surgical guide: tissue side means the side of the guide to be positioned directly adjacent the tissue of the mouth; mouth side means the side opposite the tissue side, mouth side being the exposed side when the surgical guide is positioned in the mouth for drilling and implant attachment through guide holes in the guide.

2. Traditional Manual Technique to Make and Install Dental Prostheses One basic prior art technique for creating and attaching dental prostheses is described herein and illustrated in Story Board A attached hereto as Appendix A. With this procedure an implant is secured in the jaw bone where a tooth is missing or is to be replaced, an abutment is secured to the implant and the final prostheses is secured to the abutment. Implants are typically installed so that the top of the implant or collar of the implant is flush with the bone and below the gum tissue. The collar of the implant has internal threads that receive a screw to hold an abutment or prosthesis. The collar also has an internal or external coupling or an axial keying feature such as a triangular, hexagonal or octagonal in cross-section that allows a driver to securely engage the implant to be screwed into the bone. This feature can also be used to lock the rotational position of an abutment or prosthesis secured to the implant.

Angled abutments can produce a more aesthetic result by allowing location of the prosthesis in the ideal position relative to other teeth, even if the supporting bone is not directly beneath the prosthesis. Angled abutments also allow the surgeon to use the strongest available part of the bone to support the implant even though it may not be directly beneath the prosthesis.

When replacing a single tooth it is critical that the prosthesis mounted in its initial rotational orientation, is secured from later rotating away from this orientation. This is not an issue when multiple adjacent teeth are replaced, because the replacement teeth are joined together in a single prosthesis and thus cannot rotate relative to each other. To properly orient a prosthesis, a recording of data defining the rotational position of the implant is necessary to be used for construction of an angled abutment, because angled abutments and prostheses are constructed and fitted to a model before they are placed in a patient. The prosthesis will align properly in the patient's mouth only if the analog, when the prosthesis is made, has the same position and has the same rotational alignment in the model as the final implant has in the patient's mouth.

The prior art procedure includes taking an impression (casting) of the patient's mouth, after the implant has been placed. During the impression process the position of the implant is recorded, and then a transfer post is attached to the implant with a coupling that bars relative rotation of the transfer post relative to the implant. Thereafter, casting material is applied. When the casting material has set the impression with the imbedded transfer post is removed from the patient's mouth and is then typically sent to a dental lab. At the lab an analog is attached to the transfer post, and casting material is poured into the impression and around the analog. When the material is set, the impression and transfer posts are removed from the casting, leaving a model of the patient's mouth with the analog in the same position (including rotational) as the implant is in the patient's mouth. The abutment and prosthesis are then constructed and fitted to the model. When complete, the prosthesis is returned to the dentist and installed in the patient's mouth.

This traditional technique is illustrated schematically and pictorially in FIGS. A1-A12 in the above-noted Story Board A of Appendix A, which shows a succession of stages or steps described below. The illustrations of these steps are preceded by FIG. A which shows as the conclusion of these steps, a prosthetic crown attached to an abutment attached to an implant in a patient's jaw bone.

FIG. A1 illustrates a patient's jaw with a missing tooth.

FIG. A2 indicates drilling a hole in the bone to receive an implant. FIGS. A3 and A4 show placement of the implant.

FIG. A5 shows installing a transfer post into the top of the implant, the top of the transfer post extending upward to the vicinity of the top level of the adjacent teeth.

FIG. A6 shows that an impression is made of the area of the implant and the adjacent teeth on either side of the area of the implant. The impression includes recesses representing the adjacent teeth, the area of the implant and attached to the impression is the transfer post.

FIGS. A7 and A8 show that the impression, with the transfer post included, is removed from the mouth and sent to a dental laboratory. Here, an analog is attached to the exposed top of the transfer post exposed above the surface of the impression, the analog simulating the implant.

FIG. A9 shows that said impression, which includes the exposed top of the transfer post and the analog attached to said transfer post, is cast, thus creating a "model" of the patient's relevant mouth structure with the attached analog. The impression includes a series of recesses which represent negative spaces corresponding to the positive shapes of existing teeth.

FIG. A10 shows that a model is cast from the impression. The result is a model of the patient's teeth including the space of the missing tooth and the attached analog. Now the model is used by a lab technician to build an appropriate abutment and prosthesis.

FIGS. A11 and A12 show that later this abutment and final prostheses are attached to the patient's mouth.

The final prosthesis may cooperate with (a) a straight line abutment whose axis is generally aligned and coaxial with the implant, or (b) an angled abutment which allows a prosthesis to be fixed in a patient's mouth along an axis which differs from the axis of the implant.

3. Prior art computer aided Rapid Replacement Method—
If a patient does not require angled abutments and does not have a single tooth replacement that needs to be rotationally secured, the process can be done more rapidly with the computer aided procedure commonly known as the "Rapid Replacement Method". Here, a surgical guide can be used to construct a model and prosthesis prior to the surgery for installing the implants. The dentist then uses the same surgical guide to perform the implant placement surgery. After the surgery, but in the same visit, the abutments and implants are attached, and a patient can leave the dentist's office with a temporary or final prosthesis. Thus, the patient can have all the surgery and implants in a single visit.

The above-noted computer aided Rapid Replacement Method includes a succession of stages and/or steps, as follows.

An impression is taken of the patient's upper and lower mouth, typically with a tray positioned adjacent the teeth and gums. From the impression a denture is made, to which is added radio opaque markings that will be highly visible in a CT scan and will identify specific locations to facilitate computer aided surgical planning for drilling locations.

A CT scan is taken of the patient's mouth and of the radio opaque denture, to show the underlying jaw bone structure and existing teeth and problem area.

With computer software and input from the surgeon a surgical guide is designed and created which indicates optimum choices of bone and optimum locations and angular alignments for drilling and placement of implants. The surgical guide made directly from the computer developed data, includes a tissue side corresponding generally to the shape and contour of the patient's upper or lower mouth, and an opposite mouth side, peripheral edges and drill guide holes in the optimum locations relative to the existing jaw bone structure and at predetermined locations relative to said peripheral edges and having predetermined angular alignment relative to said tissue side surface. Drill guide sleeves are situated concentrically in said drill guide holes.

Various abutments are fitted to the model that correspond to each of the implants which are intended to be installed after drilling. Then a temporary or final prosthesis is made to fit the abutments of the model, this prosthesis to be later attached permanently in the patient's mouth.

The surgical guide is then secured (temporarily) to the patient's mouth, and holes for the implants are drilled through the guide sleeves of the surgical guide. Next, the implants are inserted through the guide sleeves of the surgical guide and into the holes drilled in the bone for the implants, and the implants are screwed into place, and the drill guide is removed. The abutments are attached to the implant and a temporary or final prosthesis is attached to the abutments.

A deficiency in this Rapid Replacement method is that it is not suitable for patients who require angled abutments or for patients who need single tooth replacements that require rotational stability via the implant. The reason for this is that the current surgical guides do not indicate the intended rotational position of the implant. Without this indication the rotational alignment of the analog used in the construction of the model and the abutment and prosthesis cannot accurately or reliably correlate to the rotational alignment of the implants that are placed in the patient's mouth.

When used for the Rapid Replacement Method, the existing surgical guides are only suitable for screw retained prostheses where multiple straight abutments are used. Computer generated guides can still be used for angled abutments or single tooth replacement, but the abutments and prosthesis cannot be created prior to the surgery to install the implants.

II. OBJECTS AND SUMMARY OF THE NEW INVENTION

A first object of this invention is to allow an oral surgeon to utilize and take advantage of the Rapid Replacement method for situations including replacement of single or multiple teeth and replacement using straight or angled abutments, and thus not limited to prostheses for multiple teeth and to prostheses employing non-angled abutments.

Another object is to provide a technique for determining and employing optimal use of the patient's bone structure in his/her mouth.

An additional object is to provide a technique and apparatus for design, construction and installation of dental prostheses that is quicker, easier, more accurate, more secure and less expensive than prior art techniques and apparatus.

A further object is to provide a procedure to produce optimal aesthetic results in connection with creating and installing dental prostheses.

A still further object is to achieve optimal reliability of the resulting prostheses.

Additional objects are to optimize the use of the oral surgeon's time and minimize the time for the patient in surgery, and to minimize time and cost of creating surgical guides and prostheses.

An additional object is to provide a rotational orientation mark on the surgical guide for each implant, so that when the implant is installed through the drill guide hole, it can be set at a predetermined rotational orientation so that the abutment and prosthesis attached to said implant will automatically have the correct rotational orientation that was determined when, with the CT scan, the design of the implant and prosthesis and surgical guide were established.

It is a further object that such orientation mark on said surgical guide may be on the drill guide sleeve or on the tissue and/or mouth side. Also, the implant driver which automatically engages the implant and/or the implant fixture mount in a predetermined relative rotational orientation, because of a splined or other coupling with the implant, could have its own mark, so that the said driver is rotated until its mark corresponds to the mark on the drill guide; this will automatically orient properly the implant driven by the driver.

The reference marking for ultimate proper orientation of the implant, abutment and prosthesis may begin during the forming of the surgical guide wherein the marks are established by the surgeon when the "virtual" implant is positioned with the software or by the software. Alternatively, the marks can be manually added to the guide prior to, or as a part of the model construction process. Later the analog and/or the analog mount made to simulate the implant will have a corresponding mark, which may be point of a triangle or other shape corresponding to an apex of the axial keying recess. Such recess may be hexagonal or other keyable shape matching the keying shape of the implant. When the analog is accorded the correct orientation as established originally by the virtual implant or by other means, then the final abutments and prosthesis constructed from the analog will similarly have the correct orientation. A principal object is thus to have the final prosthesis not only installed at the designed optimal orientation but to have the installation take place very quickly, easily and accurately, with minimum time required of the surgeon and minimum surgery time experienced by the patient.

The surgical guide, as described herein, has the analogs attached at the proper orientations, and from this a model is cast replicating the patient's upper or lower mouth which includes the embedded analogs. Abutments and prostheses are formed for temporary attachment to the analogs and later attachment to the implants that will be placed in the patient's mouth.

In order to properly orient an analog mount and thus the keyed analog to the surgical guide, a mark on the mount needs to be identified and matched to a corresponding mark on the guide. Such mark on the mount may be on an end face thereof, or may be a radially extending rib, or may be a radial groove receiving a rib extending from the guide in the vicinity of a drill hole.

As described in greater detail later for the preferred embodiments, only the mouth side of the surgical guide will be exposed and visible to the surgeon. The new orientation system works because orientation for each prosthesis is determined and coded into the guide based upon the early CT scan and use of virtual implants. Later, a surgeon is able to very quickly, easily and accurately conduct the drilling and secure the implants and finally the abutments and prosthesis in the previously designated orientation. Commonly, a temporary prosthesis is installed initially to allow time for healing of the implant surgery, and later the permanent prosthesis is installed.

In the new method of this invention a new surgical guide providing drill holes location and orientation, is made and used. At each drill hole location in the surgical guide an index mark on the mouth side of the guide and/or a corresponding index mark on the tissue side of the guide is established as a reference point for the intended rotational position of the implant. The marks can be either on the metal sleeves that are liners for the drill holes or on the surrounding material that comprises the guide, or both. Such marks appear at least on the mouth side, if marking both sides is not feasible.

When the technician in the dental laboratory creates a model, the analogs are rotated until they are aligned to the index marks on the guide. The technician is then able to create custom abutments and prostheses on this model that will align with the actual implants, when such implants are later placed in the patient. The technician then constructs a temporary or final prosthesis.

In the surgical implant operation the surgeon utilizes the surgical guide to drill holes into the patient's bone. An implant driver is used to screw the implants into the patient's bone through the holes in the surgical guide. The implant driver has a mark that correlates to the anti-rotation feature on the implant collar. The implants are screwed into the patient's bone until the implants have reached the proper depth and the index mark on the implant driver lines up with the index mark on the surgical guide. The guide is then removed form the patient's mouth, and the custom-made abutments are then placed into the implants. These implants are in the same rotational position in the patient's mouth as the analogs were on the model, and the custom abutments are in the same rotational position in the mouth as they were on the laboratory model.

Advantages of this procedure to the patient are numerous and significant. The patient experiences only a single surgery session, and such session is reasonably brief. The resulting prostheses has improved reliability and reduced cost. The patient leaves the surgery with a cemented temporary prosthesis to be used until suitable healing of the area occurs. Thereafter, the abutments will be ready to received cemented final prosthesis.

These implants are potentially less prone to failure because angled abutments allow them to be placed in the best available bone, regardless of the axial orientation required by the prosthesis.

This invention provides significant advantages to the surgeon who can use the Rapid Replacement method without limitations on the type of abutments that can be considered. Further, the surgeons can use a cemented prosthesis rather than a screw-retained prosthesis which is more difficult to fit and is aesthetically inferior to cemented prosthesis.

The new invention is an improvement over prior art drill guides, and in particular overcomes the problem where current surgical guides have metal sleeves that line the holes in the guide, and fixture mounts or implant drivers fit through these holes with very little clearance. After the implant has been driven to the desired position the fixture mount can be difficult to remove from the guide sleeve. The guide sleeves have notches at the top, so that if a fixture mount becomes jammed in the guide sleeve, a tool such as a small screw driver will be inserted into the notch between the fixture mount and the sleeve. The tool can then be manipulated to apply force between the implant driver and the guide sleeve and cause them to release from each other.

The new invention improves over the Rapid Replacement computer aided technique in a variety of ways, including speed, accuracy, ease, convenience and better use of the surgeon's time and less time for the patient in surgery. The computer aided technique is normally used for single prosthesis and/or prosthesis using angled abutments. The new method can utilize the computer system without being so limited, as follows:

a) the computer aided system creates a virtual model of the mouth initially without taking an impression, b) from the virtual model a surgical guide is created with information for drilling and implant placement, and c) later a drill guide is created using a steriolithography process, and the abutment prosthesis is made. The drill guide will have the additional feature of a depth stop for the drilling and for placing the implants.

A particularly important benefit with the new invention is that in a single sitting for the patient, the dentist will drill, install the implants, the abutments, and the temporary or final prosthesis. With this invention the rotational orientations for the implants are established and recorded onto the drill guide for later use when the implants and abutments are placed. This is achieved in part by a novel marking or keying feature which begins at a production step, in contrast to prior art methods for which surgeons either concluded that the computer aided technique was simply not applicable to a prosthesis that required an angled abutment or to a single tooth replacement prosthesis, or used the surgical guide only to place implants but not to construct the model onto which the abutments and prosthesis are constructed.

The new invention allows the best of two prior art procedures which are normally independent and mutually exclusive. The prior basic implant procedure requires many manual and time consuming custom stages, and the high speed computer aided Rapid Replacement technique is limited to multiple prosthesis and non-angled prosthesis. Prior surgical guides did not indicate the appropriate rotation of the implant. In the new invention the surgical guide incorporates all relevant information for drilling, and implant placement and obviates the need for an impression to be taken between the installation of the implants and the construction of the prosthesis.

The present invention includes a new surgical drill guide, a method of making the new surgical drill guide, a method of installing dental implants and particularly a method of installing dental implants which employs the new surgical drill guide, and a method of making a model or mouth replica which employs the new surgical drill guide.

A first of the various embodiments of this invention is defined as a surgical drill guide for installing dental implants with predetermined angular alignment and rotational orientation for a dental prosthesis, comprising:
  a. a base part formed to correspond generally to the shape and contour of a patient's upper or lower mouth, said base part having peripheral edges and having opposite tissue and mouth sides and at least one hole extending through said base part from said tissue side to said mouth side,
    each of said drill guide holes having a central axis at a predetermined angular orientation relative to said mouth side and having lateral location relative to said peripheral edges, and
  b. a set of rotational position indicators on said tissue and mouth sides respectively of said base part for each of said drill guide holes, said rotational position indicators of each set being at the same rotational position about said central axis of said drill guide hole.

A second variation of the various embodiments is a method for making a surgical drill guide, comprising steps:
  a. taking an impression of the patient's upper or lower mouth,
  b. from said impression producing a denture replica of the patient's teeth and gums represented by said impression,
  c. attaching radiopaque markings onto said denture replica to indicate designated parts of said denture replica,
  d. taking a CT scan of the patient's mouth and of said radiopaque-marked denture replica in the patient's mouth to show the jaw bone structure in relation to said denture replica,
  e. with computer software and data from said CT scan, designing a surgical drill guide which indicates optimum locations and angular alignments in said jaw bone for drilling and installing dental implants, and
  f. from said drill guide design forming a surgical drill guide which includes opposite tissue and mouth side surfaces and drill guide holes which extend through said surgical drill guide from said mouth side to said tissue side surfaces at said optimum locations and angular alignments.

It is believed that the present invention will be better understood from the following description of preferred embodiments, taken in conjunction with the accompanying drawings, in which like reference numerals identify identical elements and wherein:

III. BRIEF DESCRIPTION OF THE DRAWINGS

FIGS. 1a-1m comprise a storyboard illustrating the steps or stages for practicing the present invention. FIGS. 1n, 1p, 1q, 1r and 1s are fragmentary schematic front perspective views which illustrate in enlarged and further detail, the steps of drilling and installing an implant of FIGS. 1k-1m.

FIG. 2a is a top perspective view of the mouth side of a first embodiment of a new surgical guide, FIG. 2b is a perspective view of an analog assembly for use in the surgical guide of FIG. 3a, FIG. 2c is an exploded perspective view of the analog assembly, FIG. 3a is a top perspective exploded view of the tissue side of a surgical guide of FIG. 2a adapted for making a model, FIG. 3b is similar to FIG. 3a but rotated about 90°, FIG. 4a is an exploded top perspective view of the surgical guide of FIG. 3a and an implant being installed through said surgical guide, FIG. 4b shows the guide of FIG. 4a with the implant driver engaged and driving an implant, FIG. 5 is a top perspective view of a second embodiment of a surgical guide similar to that of FIG. 2a with alternate analog mounts, FIG. 6 shows a third embodiment of a surgical guide with a still different alignment keying structure, FIG. 7 shows a fourth embodiment of a surgical guide with a still different alignment keying structure, and FIG. 8 is a perspective view showing various embodiments of surgical guide sleeves with rotational position indicators thereon.

IV. DETAILED DESCRIPTION OF THE PREFERRED EMBODIMENTS

Referring now to the drawings, FIGS. 1a-1m on Sheet 1 illustrate the succession of steps or stages of the new invention, as described in detail below.

FIG. 1a shows an impression being taken of the patient's lower mouth 10. This step illustrates a tray 11 for taking the impression positioned adjacent the lower teeth and gums.

FIG. 1b shows a denture replica 12 of the lower teeth and gums produced from the impression taken in FIG. 1a. Radiopaque markings 13 associated with specific implant locations are added for the next step.

Figure 2A:
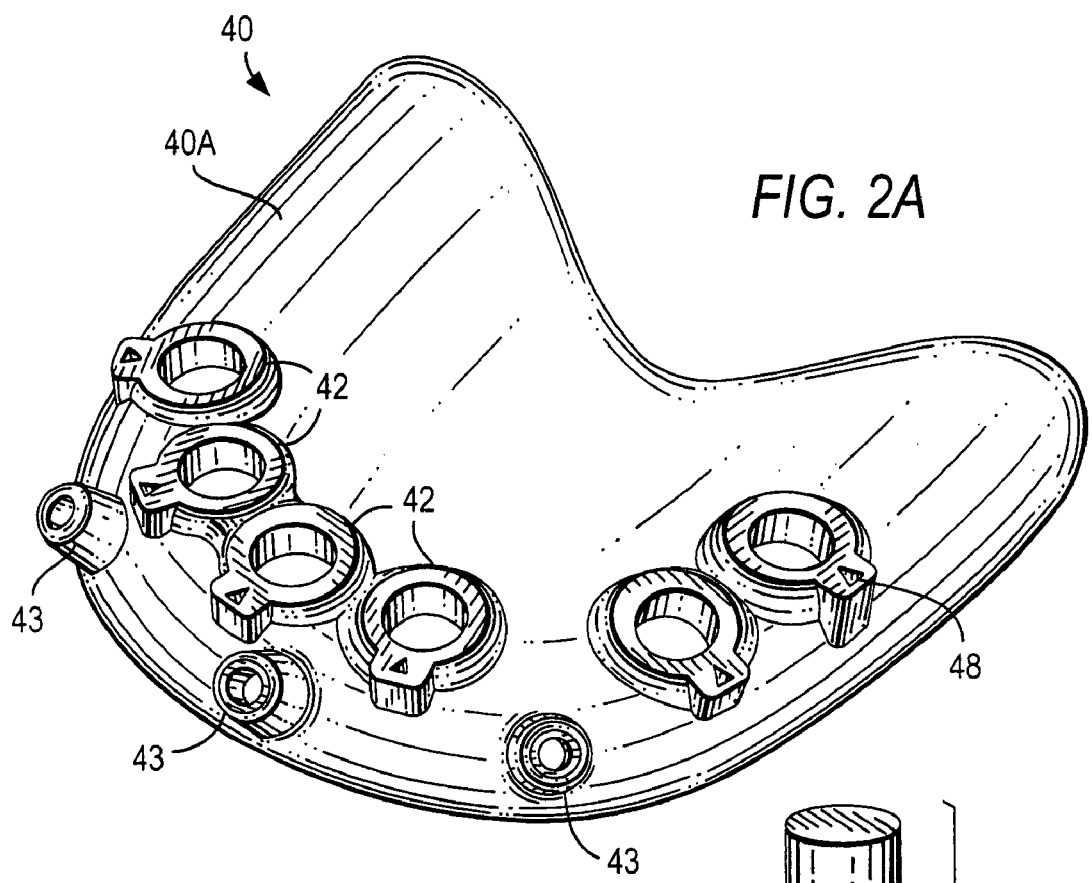

FIG. 1c indicates that a CT scan is taken of the patient's mouth and radio opaque-marked denture replica, to show the underlying bone structure and existing teeth and problem areas.

FIG. 1d indicates that with known computer software and hardware and the CT scan data and input from the surgeon, a virtual surgical guide 14 seen in monitor 15 is designed and created which indicates optimum locations and orientations in supporting bone for drilling and placement of implants.

FIG. 1e shows the mouth side 15 of the surgical guide 16 that is made directly from the computer developed data that includes "virtual implants", namely simulations of implants that will be installed later. This surgical guide 16 includes proper dimensions and orientation for fitting exactly into the patient's mouth in the correct location relative to the existing bone structure and existing teeth. Orientation marks 19A are established on the mouth side 15 of the surgical guide (see FIG. 1e), and corresponding orientation marks 19 are established on the tissue side 17 of the surgical guide.

FIG. 1f shows the tissue side 17 of the surgical guide 16 of FIG. 1e, with analogs 18 mounted and aligned to orientation marks 19 on the tissue side 17 of guide 16. A model or mouth replica 21 is created by applying casting material 20 onto said surgical guide, and subsequently removing said cast model 21 from said surgical guide. For each analog there is an index mark 19A on the tissue side 17 at the same rotational orientation as a mark 19 on the mouth side 15 of the surgical guide.

FIG. 1g shows the model 21 cast from the surgical guide.

FIG. 1h shows the model 21 of FIG. 1g with analogs 18 remaining embedded and not visible in the model, and abutments 22 attached to the analogs. Per FIG. 1f each analog is mounted with the proper predetermined orientation according to marks 19. Per FIG. 1h each abutment becomes automatically property oriented because it is keyed to an analog that was previously set with the proper orientation.

FIG. 1i shows the temporary or final prosthesis 23 made to fit the abutments 22 of model 21 of FIG. 1h.

FIG. 1j shows the surgical guide 16 secured (temporarily) to the patient's mouth and ready for drilling.

FIG. 1k indicates that the holes for the implants 26 are drilled with drill 24 through the drill guide sleeves 25 of the surgical guide 16, and installation of implants 26 (not visible in this figure) will follow.

FIG. 1l shows further installation of said implants through the holes 27 in sleeves 25 of the surgical guide and into the holes drilled in the bone for the implants. With the implant driver 28 implants are screwed into the drilled holes and rotated to correct orientation when the index mark 29 on the driver matches the index mark 19A on the drill guide. Because of the keying of driver 28 to the implant 26 and of the abutment 23 to the implant 26, the abutments and prosthesis 23 are keyed to automatically have the correct orientation. The driver 28 may employ an intermediary fixture mount 32 (further illustrated in FIG. 1q) to help install each implant, where such fixture mount has its own index guide mark 33 instead of the driver's index mark 29.

FIG. 1m shows that the surgical drill guide has been removed, the abutments installed, and a temporary or final prosthesis 31 is being to the abutments.

The steps 1k-1m are illustrated more clearly in the enlarged and more detailed FIGS. 1n and 1p-1s, as follows.

FIG. 1n is a fragmentary top front perspective view showing the surgical drill guide 16 placed in the lower mouth with the drill 24 positioned and a typical hole 40 drilled in the jawbone 41.

FIG. 1p is a fragmentary front perspective view showing the surgical drill guide 16 still in place, the drill removed and the drilled hole 40 visible in the jawbone 41.

FIG. 1q is a fragmentary front perspective view showing the surgical drill guide 16 still in place, and an implant 26 being driven downward into the drilled hole 40 by a driver 28 with the rotational position indicator 30 visible on the mouth side 15 of the drill guide 16 and corresponding index marks 29 visible on the implant driver 28.

FIG. 1r is a fragmentary front perspective view showing that the surgical drill guide has been removed, and an abutment 22 has been attached to the top of the implant 26, secured by screw 42 with the abutment 22 automatically in the correct rotational position by virtue of the implant 26 being correctly indexed and the abutment 22 being keyed to the implant abutment. In the example illustrated here, the abutment is inclined to accommodate a particular prosthesis.

FIG. 1s a fragmentary front perspective view showing the dental prosthesis 23 or denture attached to the top of the abutment.

In the discussion above steps 1a-1e pertain to forming a drill guide, steps 1f-1i pertain to using the new drill guide to form a model of the patient's mouth and forming the new prosthesis, and steps 1j-1m and 1n-1s pertain to using the surgical drill guide to drill, install implants, and then after removal of the drill guide to install abutments and the prosthesis. The remaining FIGS. 2a-2c, 3a-3b, 4a-4b and 5-7 illustrate in greater detail different embodiments of surgical drill guides, as follows.

Referring first to FIGS. 1a-1f, when the surgical guide 16 is made using the impression 12 of the patient's mouth, the CT scan and the computer software, rotational alignment or index marks are incorporated onto the surgical guide, and then the analogs 18 are installed onto the surgical guide in accordance with index marks 19. Thereafter, the cast model 20 of FIG. 1g which includes embedded analogs 18 automatically includes "indexing" carried forward by the "indexed" analogs.

Per FIG. 1h abutments 22 are temporarily installed onto the correctly indexed analogs 18, and per FIG. In the prosthesis 23 is made to fit these abutments. That ends, for a time, the steps for making and fitting a prosthesis, which is removed for later installation. The abutments are removed now, or later, for eventual installation onto the implants after they are installed in the patient's mouth. These abutments, or other but identical abutments, may be used. The next sections herein describe different embodiments of surgical guides and use thereof.

A first embodiment of the new surgical guide 40 is shown schematically in FIG. 2a, having a mouth side or exposed side 40A of base part 41. Drill guide sleeves 42 are positioned and oriented optimally in regard to the bones to receive implants, and guide holes 43 are provided for receiving nail or other fasteners to temporarily secure the surgical guide to the mouth for the drilling and implant installation procedure.

Figure 2B:
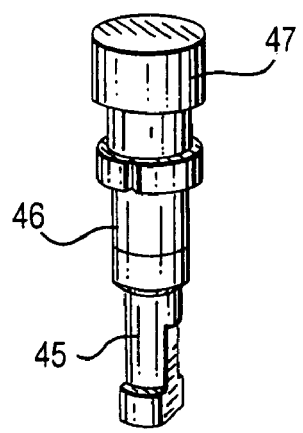
Figure 2C:
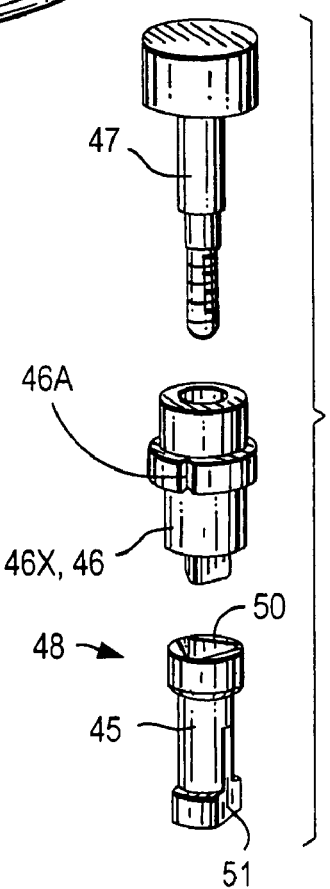

FIG. 2b shows an analog assembly 44, and FIG. 2c shows an exploded view of said analog assembly. This assembly consists of analog 45, analog mount 46 and attachment screw 47. The analog 45 of FIGS. 2b and 2c is typical of the analogs that would be attached to surgical guide 40 in FIG. 2a, which is then used to create a model of the type shown in FIGS. 1f-1h on Sheet 1.

As seen in FIGS. 2a-2c the new invention provides rotational markings 46A on the analog mount 46 and corresponding marks 48 on the surgical guide. In the subsequent stage each analog is positioned in a guide sleeve of the surgical guide, at which time each analog mount is rotationally oriented until its mark 46A corresponds to the pre-set mark 48 on the surgical guide. The analog 45 is automatically keyed to the analog mount 46 by the triangular recess 50 in the end of analog 45 with the triangular axial extension 46X of the analog mount. Then, via the analog mount and screw, the analog 45 is secured in the surgical guide.

Figure 3A:
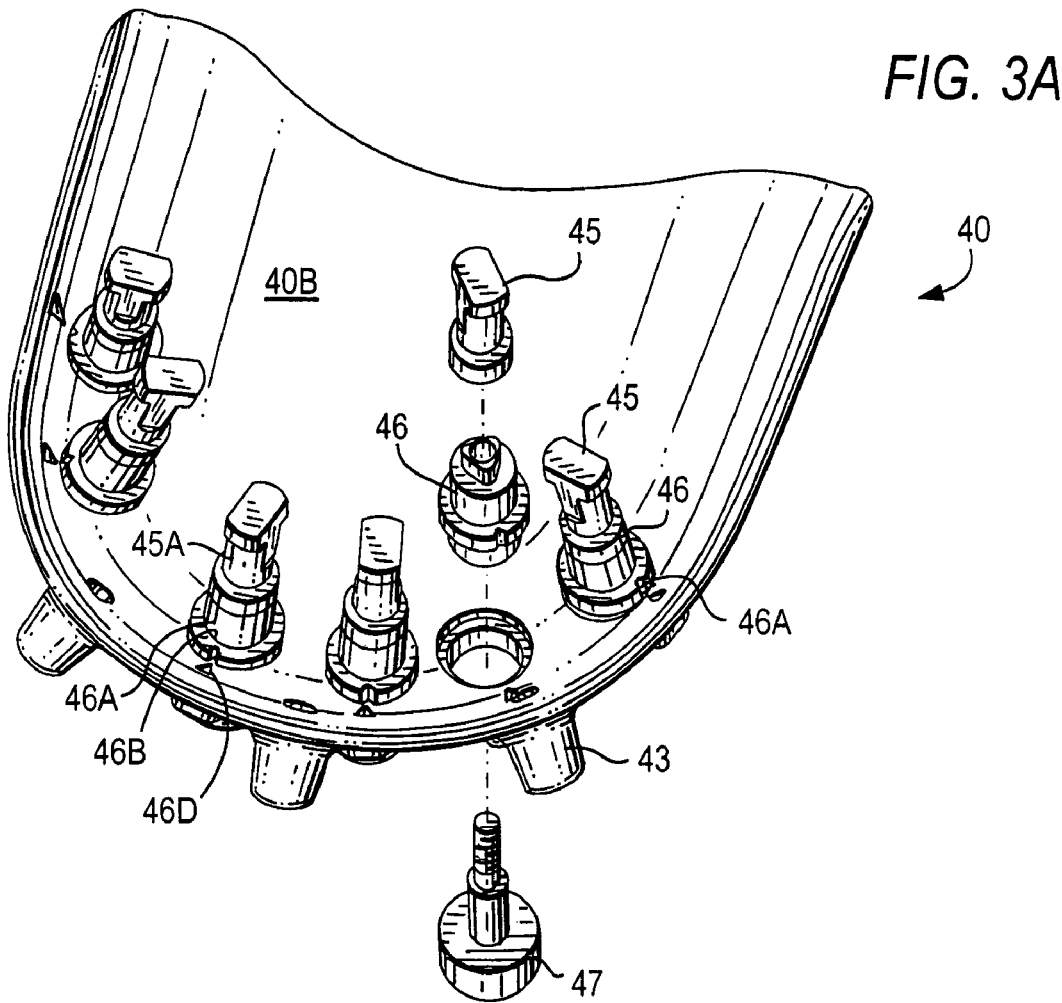

Since this surgical guide 40 will be used to create the model, analogs 45 must extend downward through the mouth side 40A (FIG. 2a) and extend outward on the opposite tissue side 40B of the surgical guide, as seen in FIG. 3a.

Each analog is situated on an x, y grid for proper location and at a direction for elevation, and at a predetermined optimum rotational orientation. Finally, each analog must be rotationally aligned so that the permanent prosthesis, when secured to the abutments, will be properly rotationally oriented about its axis.

Each analog thus has a proper position within the guide and has its own further indexing feature (internal splined bore) that will lead to proper orientation of the implant in the bone, for which the analog is a replica. Thereafter, the abutment attached to the implant and the prosthesis attached to the abutment will all have the proper rotational orientation.

Figure 3B:
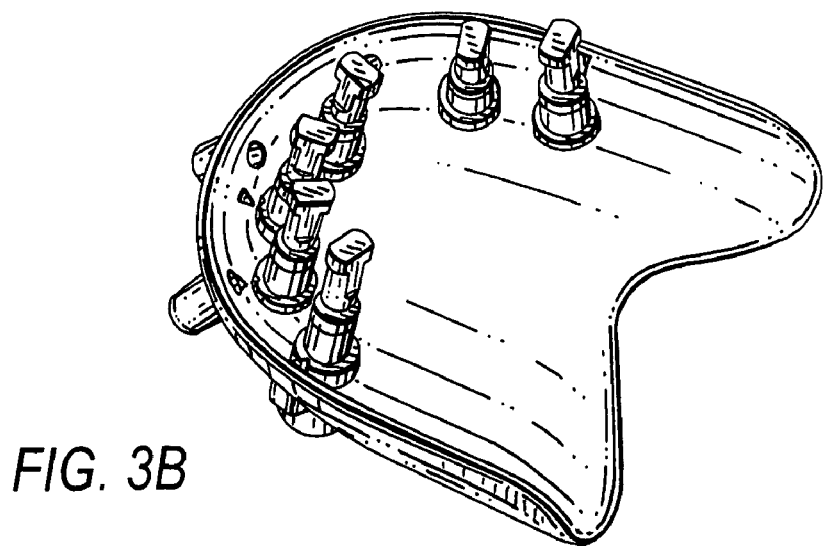

FIG. 3a indicates how typical analog mount 46A has its mark 46B aligned with mark 46D on the surgical guide 40, and analog 45A will be similarly aligned, so that the final prosthesis will have its own final alignment. FIG. 3b shows the tissue side 40B of the guide 40 of FIG. 4a rotated about 90° clockwise from FIG. 3a and with all analogs attached.

Now the surgical guide is ready to be cast, according to FIGS. 1f-1h, to create a model where the analogs create the replica recesses for the implants that will be positioned in the model and on which will be attached the abutments and the prosthesis.

Figure 4A:
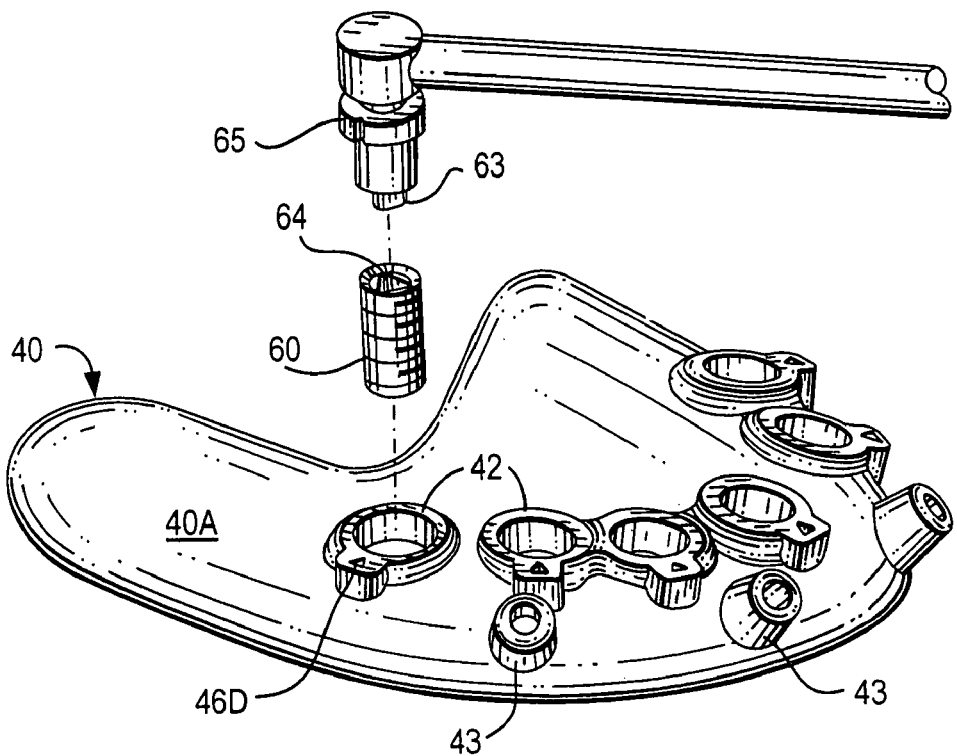
Figure 4B:
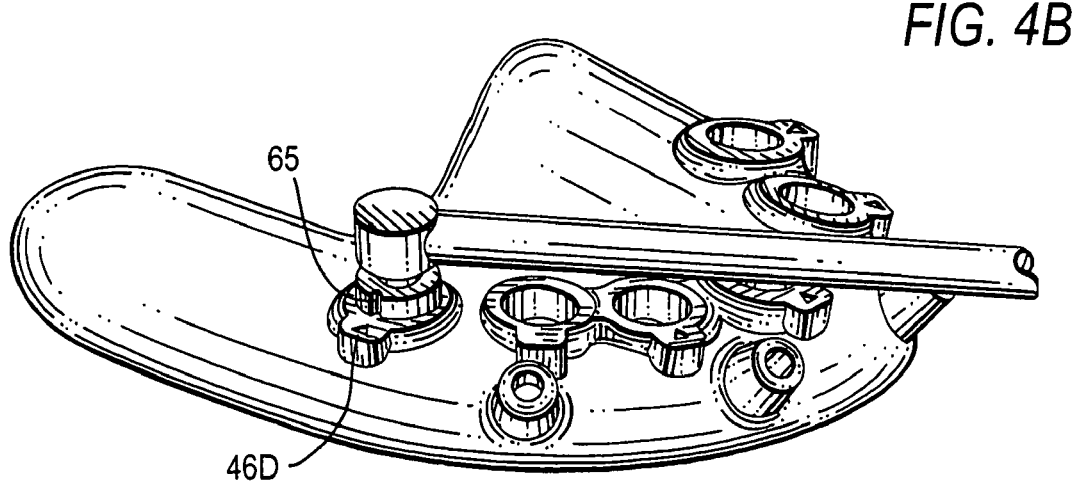

FIGS. 4a-4b indicate how installation of implants 60 takes place with the surgical guide 40 of FIG. 3b. FIG. 4a shows the mouth side 40A of surgical guide 40, with the analogs 45 all removed and the guide secured to the mouth (not shown) with fasteners through fastener sleeves 43. In FIGS. 4a, 4b it is further understood that drilling through drill guide sleeves 42 has also been completed, with each hole drilled at the proper location, angle and depth.

FIG. 4a shows a typical implant 60 being inserted through a drill guide sleeve 42 and into the drilled hole in the bone (not shown) and the implant driver 61 for installing said implant. When implant driver blade 63 of triangular cross-section is situated in triangular bore 64 in the exposed end of implant 60, the surgeon cannot then see the rotational orientation of the points of the triangular slot, which points indicate the final desired rotational orientation. However, as seen in FIG. 4b the implant driver has its own rotational marker or index mark 65 that corresponds to the now hidden point of triangular stem 63. Consequently, the implant can be screwed into the bone to the correct depth and to the correct rotational orientation.

After all the implants are similarly installed, surgical guide 40 is removed from the patient's mouth, and the prostheses are attached to the implants, as further discussed below.

Figure 5:
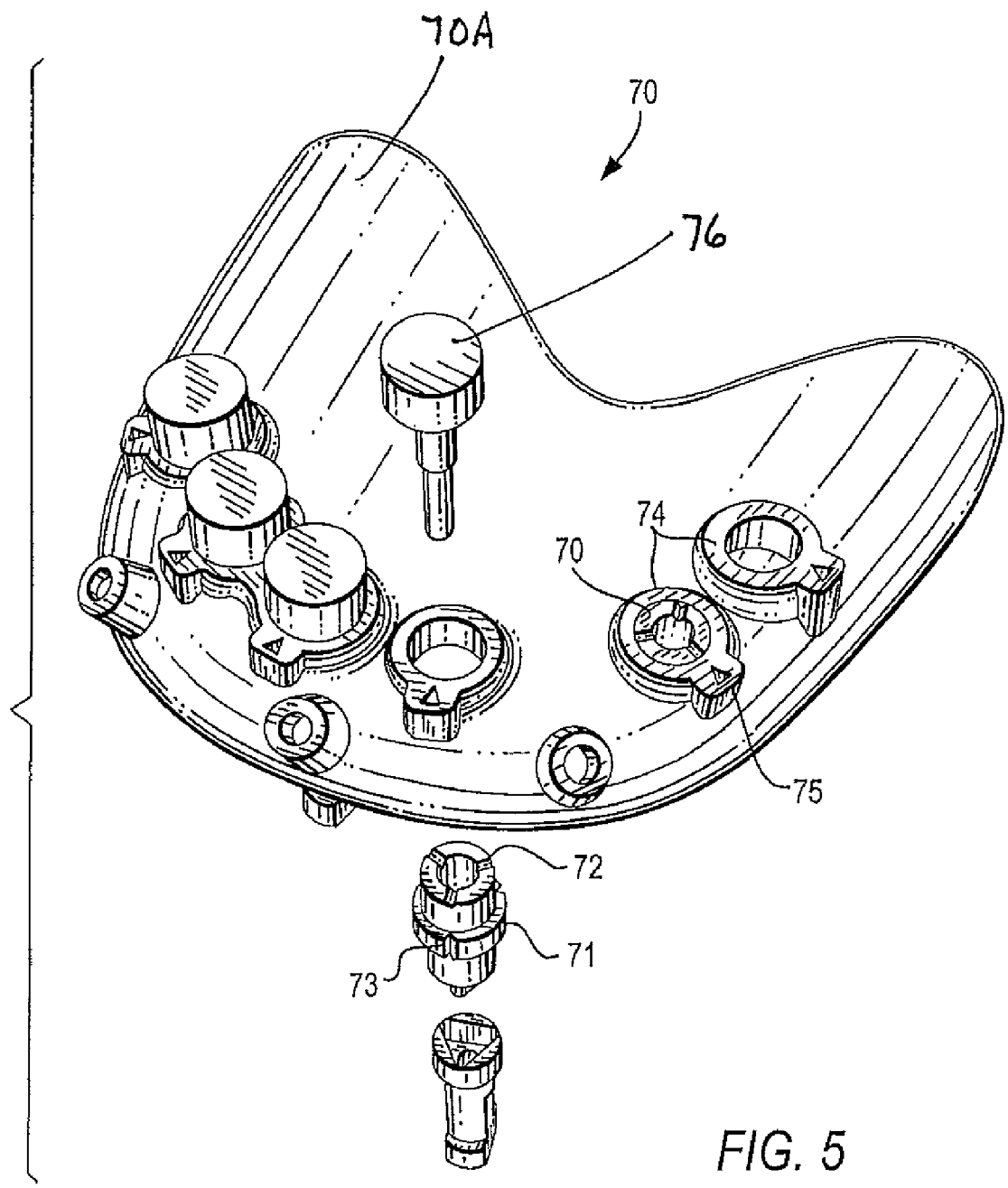

FIG. 5 illustrates the mouth side 70A of a further embodiment of a surgical guide 70. This pertains to the stage if, described above, where a surgical guide is constructed with inclusion of analogs 76, in order to then cast a model. FIG. 5 shows a variation of the technique to achieve correct rotational orientation of the analogs 76 so that the implants and their associated abutments and final prosthesis will be correctly orientated.

In FIG. 3a each analog mount 46 has marking 46B visible on the side for matching with a mark 46D on guide 40. In FIG. 5 analog mount 71 has its index marking 72 on the end face of mount 71 in addition to prior marking 73 on the sides. Analog mount 73 is ready to be situated in a drill guide sleeve 74 with its index index 72 aligned with the drill guide's own index mark 75. After such analog is properly aligned, screw 76 is installed through the analog mount and into the analog to secure it.

Figure 6:
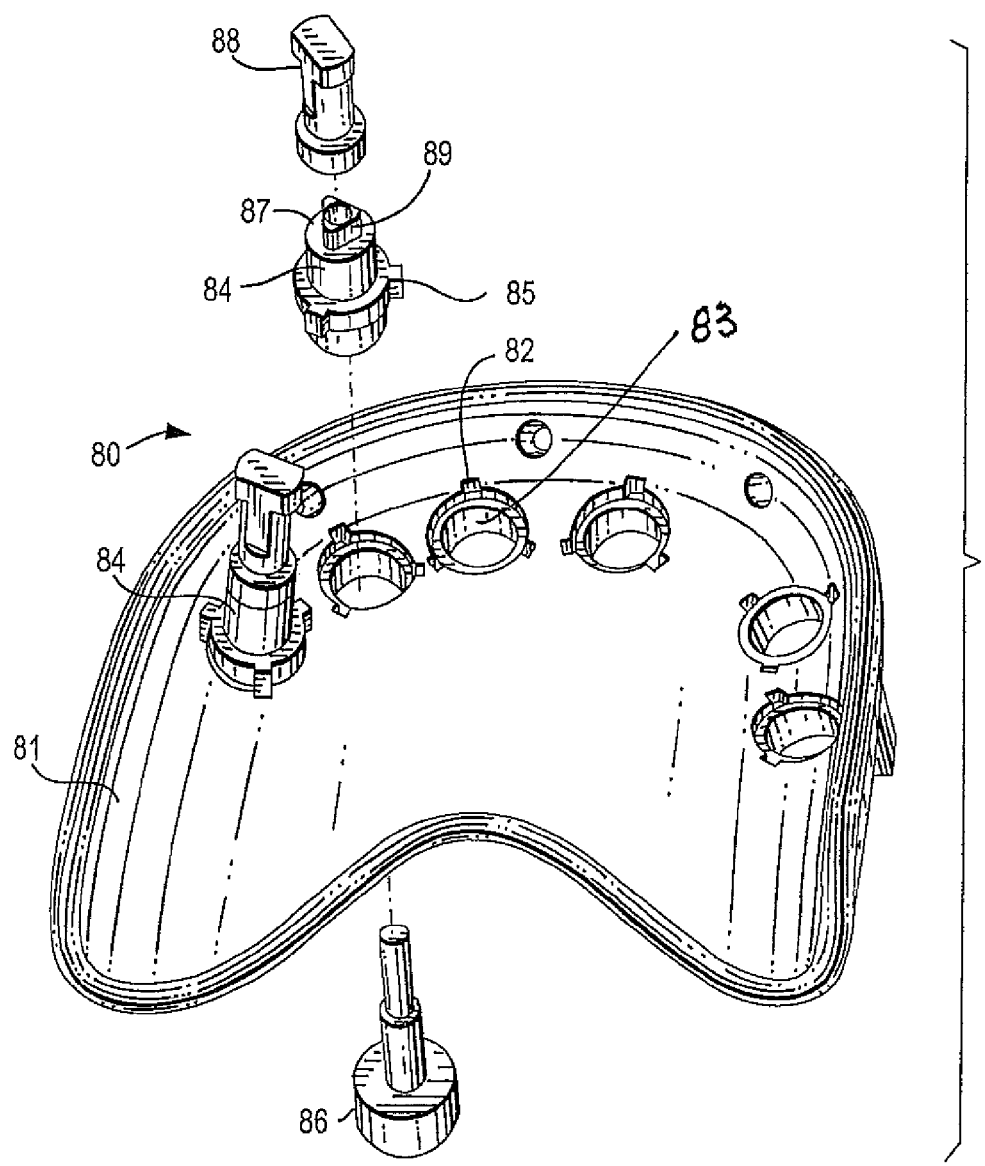

FIG. 6 illustrates a still further embodiment of a surgical guide 80 where the base 81 has its own keying grooves 82 at 120° intervals around the periphery of the hole 83 or the drill guide sleeve. When the analog mount 84 is positioned in the hole 83, its keying tabs 85 enter grooves 82 and automatically establish the correct rotational orientation of analog mount 84. Screw 86 enters from the mouth side, passes through the analog mount and enters and secures analog 88 to base 81 of guide 80. As described earlier, after analog mount 84 is secured, its exposed end 87 receives analog 88 which is rotationally oriented by key 89 at the end 87 of the analog mount.

Figure 7:
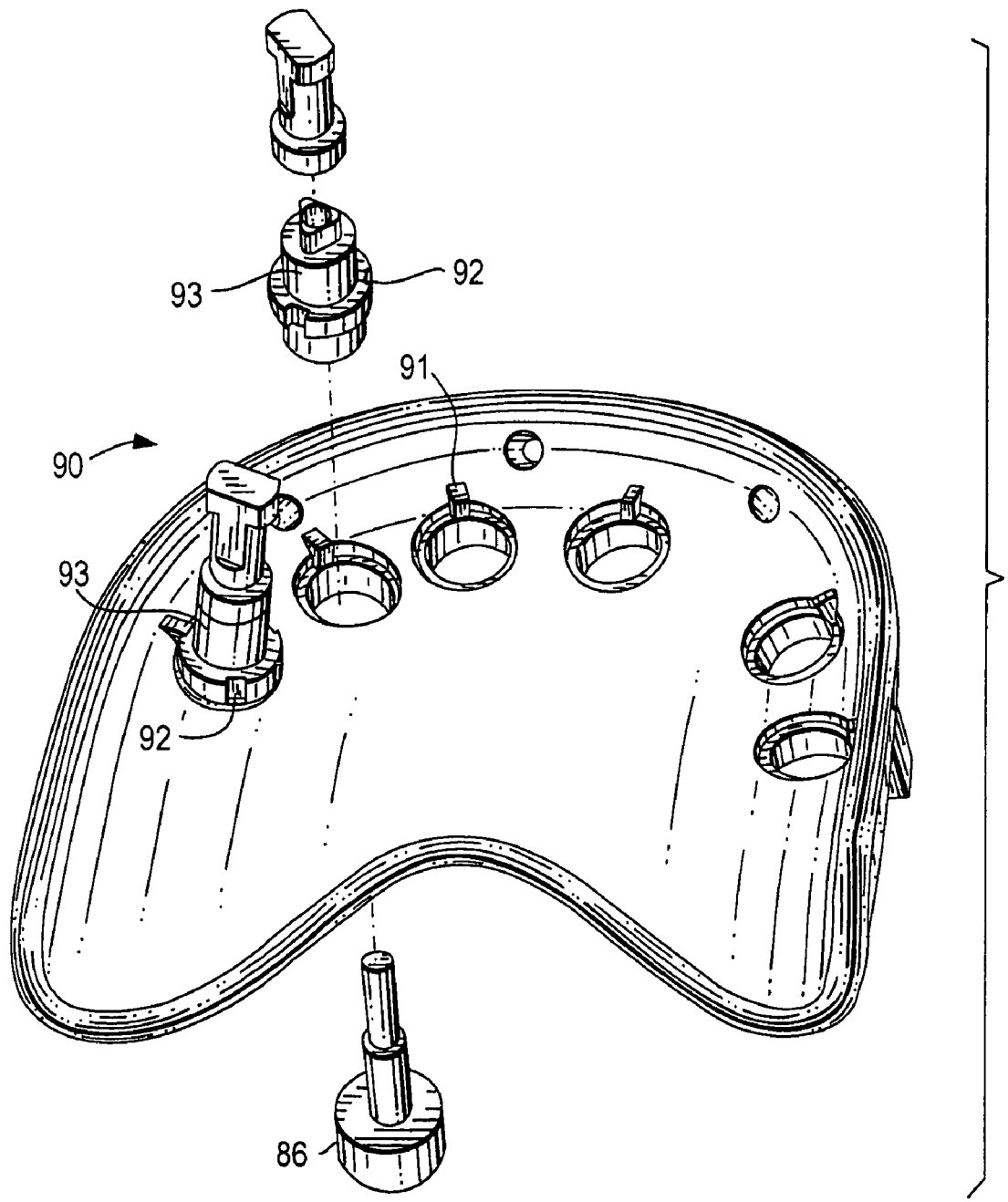

FIG. 7 illustrates a further drill guide embodiment 90 similar to drill guide 80 of FIG. 6, except that grooves 82 in the guide and keys 85 on analog mount 84 in FIG. 6 are replaced by keys 91 in the drill guide 90 and grooves 92 in the analog mount 93 respectively in FIG. 7.

A still further surgical guide embodiment similar to that of FIGS. 4a and 4b, has the same general structure, but is transparent so that a rotational position indicator on one side (tissue or mouth side) can be seen from the other side, and thus marks are not required on both sides. Such an embodiment will be defined as (a) having a rotational position indicator on said mouth side or (b) having a rotational positional indicator on at least one of said moth and tissue sides, and discernable on the other side. FIGS. 43a and 4B show the marks on the mouth side.

Figure 8:
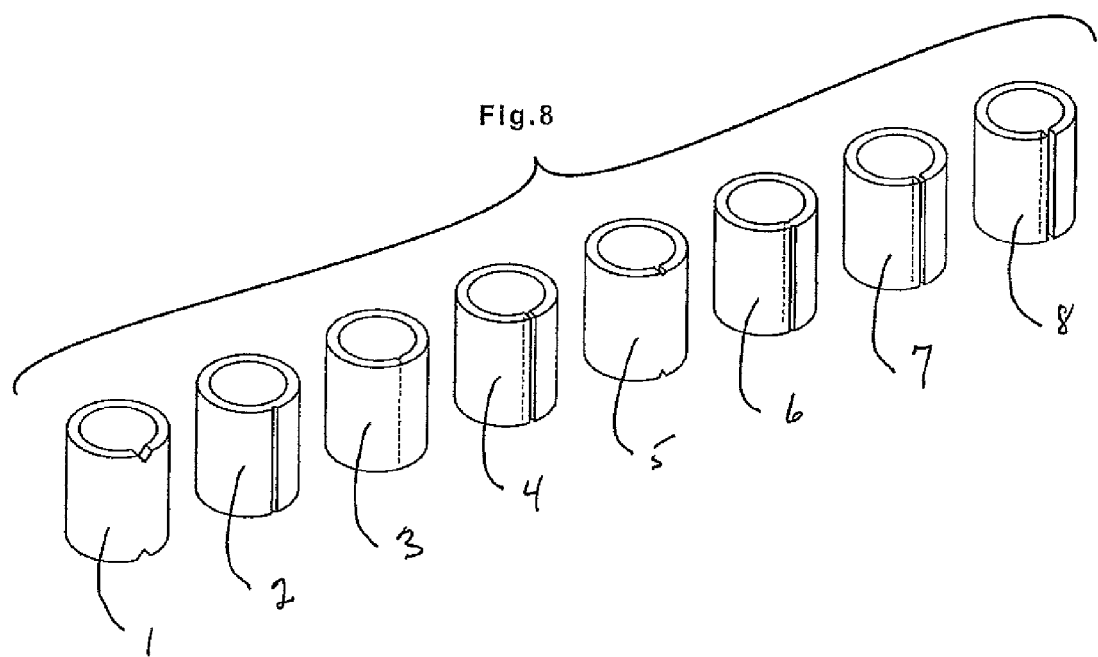

FIG. 8 shows various different drill guide sleeve embodiments, 1-8, each having coordinated rotational position marking on internal and external wall surfaces and on end surfaces, where the markings may be marks, projections, grooves, splines, etc., and where it is optional for the user to have any, all or combination of said markings, While the invention has been described in conjunction with several embodiments, it is to be understood that many alternatives, modifications and variations will be apparent to those skilled in the art in light of the foregoing description. Accordingly, this invention is intended to embrace all such alternatives, modifications, and variations which fall within the spirit and scope of the appended claims.

The invention claimed is:

1. A surgical drill guide for installing dental implants with predetermined angular alignment and rotational orientation for a dental prosthesis, comprising:
   a. a base part formed to correspond generally to the shape and contour of a patient's upper or lower mouth, said base part having peripheral edges and having opposite tissue and mouth sides and at least one drill guide hole extending through said base part from said tissue side to said mouth side, said at least one drill guide hole having a central axis at a predetermined angular orientation of said central axis relative to said mouth side and having lateral location relative to said peripheral edges, and
   b. a set of rotational position indicators on said tissue and mouth sides respectively of said base part for said at least one drill guide hole, said rotational position indicators of each side being at the same rotational position about said central axis of said at least one drill guide hole, said indicators providing a rotational position reference for an implant to be inserted in a hole drilled through said drill guide.

2. A surgical drill guide according to claim 1 where said base part further comprises a drill guide sleeve with a central bore, said drill guide sleeve situated in each of said at least one drill guide holes.

3. A surgical drill guide according to claim 2 wherein said set of rotational position indicators are on said sleeve associated with each of said at least one drill guide hole.

4. A surgical drill guide according to claim 1 wherein said rotational position indicators are markings visible in or on a surface of said base part.

5. A surgical drill guide according to claim 2 wherein said rotational position indicators are markings visible in or on a surface of each of said sleeves.

6. A surgical drill guide according to claim 1 wherein said rotational position indicators comprise projections on said tissue and mouth sides of said base part.

7. A surgical drill guide according to claim 1 wherein said rotational position indicators are keying grooves on said tissue and mouth sides of said base part.

* * * * *